Figure 1:
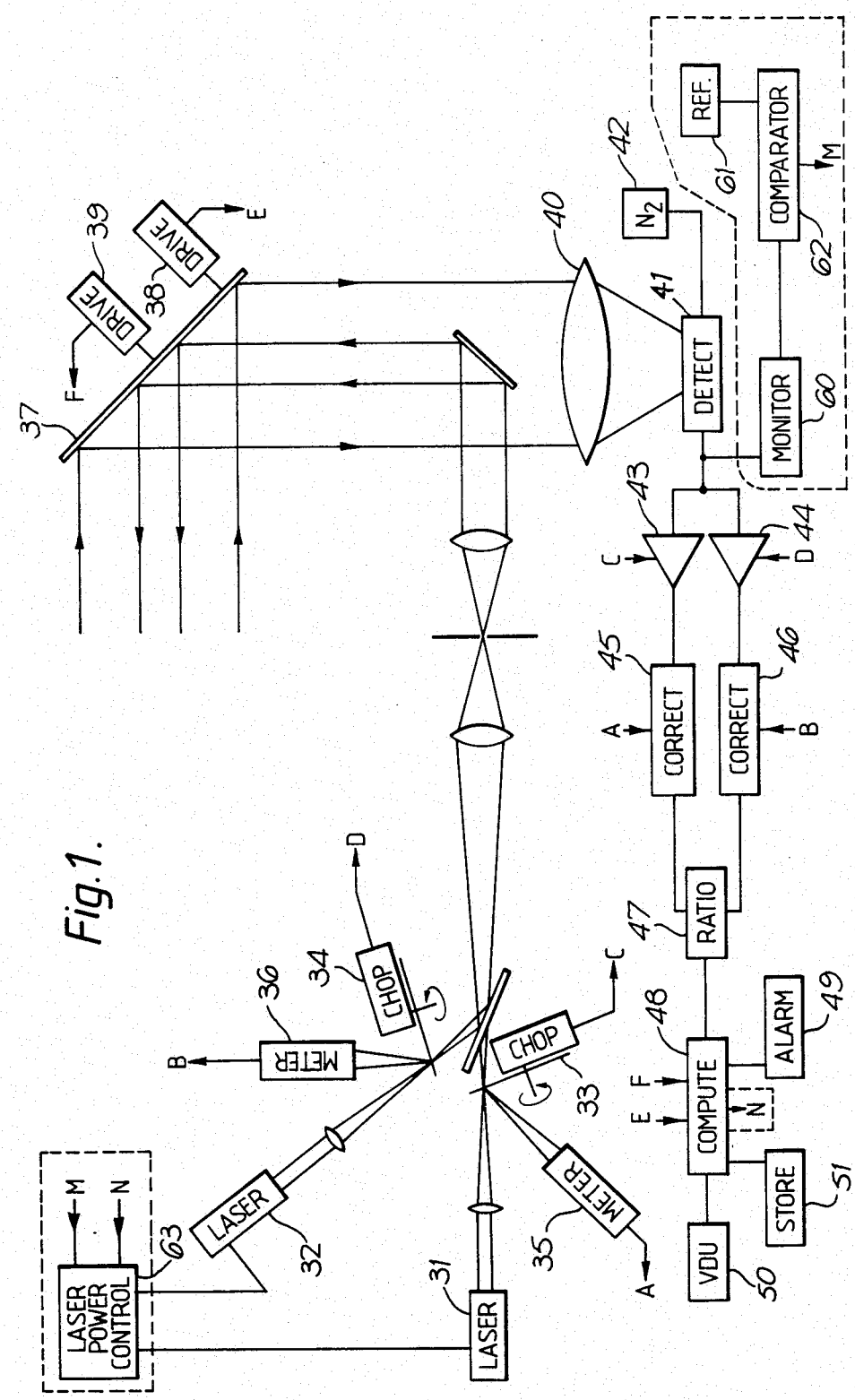

United States Patent [19]

Cramp

[11] Patent Number: 4,490,043

[45] Date of Patent: Dec. 25, 1984

[54] METHOD OF AND APPARATUS FOR MONITORING GASEOUS POLLUTANTS

[75] Inventor: John H. W. Cramp, St. Helens, England

[73] Assignee: Imperial Chemical Industries PLC, Hertfordshire, England

[21] Appl. No.: 353,418

[22] Filed: Mar. 1, 1982

[30] Foreign Application Priority Data

Mar. 2, 1981 [GB] United Kingdom ............... 8106539

[51] Int. Cl.³ ............................................. G01N 21/35
[52] U.S. Cl. ................................. 356/407; 250/339; 356/51; 356/437
[58] Field of Search ............... 356/51, 407, 409, 437, 356/438, 342; 250/339, 343, 345; 343/7.5

[56] References Cited

U.S. PATENT DOCUMENTS

| | | | |
|---|---|---|---|
| 3,361,912 | 1/1968 | Lundberg | 250/229 |
| 3,766,380 | 10/1973 | Menzies | 250/343 |
| 4,072,858 | 2/1978 | Stone | 250/205 |
| 4,146,799 | 3/1979 | Pitt et al. | 250/574 |

FOREIGN PATENT DOCUMENTS

| | | |
|---|---|---|
| 1067133 | 11/1979 | Canada. |
| 0026046 | 8/1980 | European Pat. Off. |
| 1208213 | 10/1970 | United Kingdom. |
| 1352500 | 5/1974 | United Kingdom. |
| 1430183 | 3/1976 | United Kingdom. |

OTHER PUBLICATIONS

Optics and Laser Technology, vol. 13, No. 1, Feb. 1981, C. Werner "Slant Range Visibility Determination from Lidar Signatures by the Two-Point Method", pp. 27 to 36.

Marthinsson et al., *Optical and Quantum Electronics*, vol. 12, No. 4, Jul. 1980, pp. 327-334.

*Primary Examiner*—F. L. Evans
*Attorney, Agent, or Firm*—Cushman, Darby & Cushman

[57] ABSTRACT

Laser scanning apparatus for the monitoring of gaseous pollutants (e.g. on a chemical plant) in which two laser beams having different wavelengths (one corresponding to an absorption line of the gas to be monitored) and modulated at different frequencies are combined into a single scanning beam. A portion of the scattered radiation is collected, detected and measured to give, for each chosen beam direction, the amount of the gas being monitored. The amount of radiation reaching the detector from the laser source is varied according to a predetermined programme or in response to an external stimulus, and by this means the detector can be protected against severe overload when the beam scans over positions of abnormally high reflectivity.

12 Claims, 2 Drawing Figures

METHOD OF AND APPARATUS FOR MONITORING GASEOUS POLLUTANTS

The invention relates to the remote monitoring of one or more selected gases, especially pollutants in a gaseous environment.

In the specification of our copending European Patent Application No. 80302867.9 under the same title (corresponding to U.S. patent of Becconsall et al, U.S. Pat. No. 4,426,640, issued Jan. 17, 1984), we describe a method for the remote quantitative monitoring of one or more selected gases in a gaseous environment, and also apparatus for carrying out such monitoring. The method described in that specification (which for simplicity may be referred to in this specification as "the method herein specified") comprises the steps of generating electromagnetic radiation from laser sources to give at least one detection beam containing a specific absorption wavelength of the gas or gases being monitored and at least one reference beam having a wavelength that is significantly less strongly absorbed by the gas or gases being monitored, modulating the amplitude of each of the beams with different modulation frequencies or phases, combining the modulated beams into a single beam in which the component modulated beams are substantially coincident with one another, displacing the combined beam angularly through the gaseous environment so as to direct the combined beam towards a plurality of locations sequentially and repetitively, collecting at least a portion of the radiation which is returned from each of the locations, deriving electrical signals corresponding to the intensity of the collected radiation, isolating the electrical signals corresponding to the intensity of the radiation having the aforesaid modulation frequencies or phases, and obtaining the ratio of the isolated signals corresponding to radiation collected from a detection beam and a related reference beam thereby to provide a measure of the amount of the selected gas or gases in each beam path traversed by the collected radiation originating from the laser sources.

The apparatus described in that European specification (which may similarly be referred to in this specification as "the apparatus herein specified") comprises laser sources for generating electromagnetic radiation capable of being tuned to give at least one detection beam containing a specific absorption wavelength of the gas or gases to be monitored and at least one reference beam having a wavelength that is significantly less strongly absorbed by the gas or gases to be monitored, means for modulating the amplitude of each of the beams with different modulation frequencies or phases, means for combining the modulated beams into a single combined beam in which the component modulated beams are substantially coincident with one another, scanning means to displace the combined beam angularly through the gaseous environment so as to direct the combined beam towards a plurality of locations sequentially and repetitively, means for collecting at least a portion of the radiation which is returned from each of the locations, a detector for deriving electrical signals corresponding to the intensity of the collected radiation, means for isolating the electrical signals corresponding to the intensity of radiation having the aforesaid modulation frequencies or phases, means for obtaining the ratio of the isolated signals corresponding to radiation collected from a detection beam and a related reference beam thereby to provide a measure of the amount of the selected gas or gases in each beam path traversed between the apparatus and the scanned locations, and means for indicating the amount of gas detected.

The method (and correspondingly the apparatus) described therein is useful for remote monitoring of the gaseous environments around, for example, industrial locations such as chemical plants handling toxic or inflammable gases. The degree of sophistication in the measurements which the method provides may vary considerably. In its simplest form, a measurement may only indicate that gas is present or is present at levels about a predetermined threshold so that an alarm may be sounded. Alternatively, the measurement may provide an assessment of the actual amount of the selected gas traversed by the beam when directed at each location, and apparatus is disclosed therein for displaying this on a VDU display representing the area scanned by the beam.

However, we have now found that in practice, on certain types of location, there is a real risk of overloading the detector and associated electronics. Thus when the combined beam is returned by its being scattered by buildings, roads and various mechanical constructions, for example, only a very small proportion of that leaving the laser source, reaches the detector. The latter must therefore be very sensitive. However, a practical consequence of this is that when the beam scans across a highly reflective region, the detector, or subsequent electronic equipment handling the signal derived by the detector, is liable to become overloaded. This can occur when the beam is directed at a specular reflector which happens to be accurately aligned to reflect a high proportion of the radiation it receives from the laser back towards the collector. It can also happen when objects which, while not being highly reflective in themselves, are sufficiently close to the apparatus for the collector to receive a high proportion of the laser radiation scattered by them. For these, and for other reasons described hereinafter, we now find that in certain situations it can be advantageous temporarily to extinguish the radiation or otherwise to vary the amount of radiation seen by the detector.

According to a first aspect of the present invention, there is provided a method for the remote quantitative monitoring of one or more selected gases in a gaseous environment, which comprises the method herein specified characterised by the step of varying according to a predetermined programme or in response to an external stimulus, the amount of radiation from the laser sources which is detected by the detector thereby to prevent the detected amount from exceeding a predetermined level.

A preferred method is one in which the step comprises varying according to the predetermined programme or in response to the external stimulus, the amount of radiation reaching the detector from the laser sources. This method is preferred to an alternative in which no steps are taken to vary the amount of radiation reaching the detector but in which the sensitivity of the detector is varied so that the amount of radiation detected is correspondingly varied. However, although not herein preferred, such alternative sensitivity-adjusting methods can be viable, and are described later in this disclosure.

For continuous monitoring on permanent sites, whether the locations are adjacent and merge imperceptibly so that they can be scanned by displacing the beam smoothly across them, or whether the locations are spaced apart and the beam displaced stepwise to stop briefly on individual locations, the scanning is most conveniently effected cyclically in that the beam is directed at all the various locations in a predetermined order in each cycle, the same order being retained in subsequent cycles. Any permanent regions of high reflectivity will then occur during each cycle and at the same point in each cycle, and attenuation of the radiation can then be synchronised to the scanning cycle to provide the aforesaid "predetermined programme". This can be achieved very simply, for example, by using a mechanical or electro-mechanical trip on the scanning means to actuate means for attenuating the the radiation this being particularly suited to simple two dimensional scanning. Raster scans can be accommodated mechanically by counting the lines of the raster scan, although more complex programmes can be handled more easily electronically, even when using the same basic logic as the above mechanical programmes. When using a computer for overall control, the scanning and synchronised attenuation programme may be provided very conveniently on a subroutine of the computer program, e.g. using the above logic.

However, synchronisation of the attenuation with the scanning cycle is not a solution to all problems which may be overcome by the present invention. Thus the overloading position may move within the cycle, or indeed be only temporary. Thus for example an object, e.g. a bird, may move through the laser beam very close to the apparatus, and although not particularly reflective, the scattered radiation collected may be significant due to the proximity of the object. Likewise, reflective surfaces of a passing car may cause the problem for only a very short period, e.g. within a single scanning cycle, and be completely unpredictable. Slightly longer term, but still temporary, problems can be caused, for example by scaffolding erected close to the apparatus, and shortly moved or removed. Thus use of wipers moving across the surface of the scanning mirror to keep it clean can also cause the problem of temporary overload (although we prefer to clean the mirror during a predetermined pause in the scanning cycle).

To overcome such temporary overload, or overload whose position in the cycle varies, we prefer a method which comprises monitoring the amount of radiation collected and varying the amount of radiation reaching the detector from the laser sources in response to the amount of radiation monitored, the amount of monitored radiation thus providing the "external stimulus". The collected radiation can be monitored by diverting a portion of the collected light to a separate monitoring detector. However, we prefer to monitor the collected radiation by monitoring the signal derived from the detector, as this does not cause any of the precious low-level signal to be removed for monitoring purposes, and hence lost, before reaching the detector. There are at least two approaches to the step of varying the amount of laser radiation detected, which can be taken.

One approach involves effectively shutting down the apparatus while the danger of overloading persists, and is one which, whenever the collected radiation exceeds a predetermined threshold, comprises imposing a constraint to reduce the amount of laser radiation reaching the detector to an undetectably low level, e.g. to zero, and removing the constraint after a predetermined time interval. The most appropriate threshold level will be dependent on the loading capabilities of the detector and associated electronics. The most appropriate time interval will depend on the parameters of the installation, such as frequency of highly reflective areas and rate of scan. If the predetermined time interval is too short for the returned radiation to be reduced below the threshold, the constraint will again be triggered for a further time interval. If the predetermined time interval is unduly generous, the period during which the gases are not monitored will be unduly large.

A different approach is one in which, whenever the collected radiation exceeds a predetermined threshold, the amount of laser radiation reaching the detector is varied so as to remain within a predetermined range in excess of the threshold for so long as an excess of the radiation is collected. The range is preferably narrow, and is preferably just below the level at which overloading occurs so that most measurements can take place without any attenuation of the laser radiation and yet enabling monitoring of the gases to continue even when the laser radiation is returned to the detector to an abnormally high extent.

Reduction in the amount of radiation reaching the detector from the laser sources can be achieved by blocking or diverting the radiation returned from the relevant locations, before that radiation reaches the detector. However, to avoid spurious rays of radiation scattered or diffracted by moving shutters in the receiving optical system a preferred method comprises reducing the amount of laser radiation which is directed at those locations. This may be achieved by blocking or attenuating the radiation produced by the laser sources, or by reducing the amount of radiation actually produced by the lasers, either partially or in toto. Attenuation of light produced by the sources can be effected by mechanical means, e.g. an iris diaphragm, but this can result in the ratio of the detection and reference beams being altered. Accordingly, we prefer to reduce radiation output by controlling the output of the lasers, monitoring that output before the beams are combined, comparing the output levels monitored and either adjusting the laser outputs to maintain a constant output ratio, or compensating for any variations in the ratio of their outputs when determining the ratio of the two beams in the radiation returned from the locations.

As will be realised, when the radiation is reduced in response to an increased signal from the detector, such response must in most cases be very fast. An alternative to the above-described method of reducing the amount of radiation is one which includes the step of desensitising the detector in response to an increase in its output signal. This may be complete desensitisation, e.g. by switching off the detector or an actuating bias in the detector. In this case it is preferred that the method also includes the step of sensitising the detector after a predetermined time interval. An alternative is to monitor the output of the detector and in the event of the detector output rising beyond a predetermined threshold, to adjust the sensitivity of the detector with changes in detector output such that the output remains within a predetermined range. This is most conveniently a narrow band immediately below the onset of overloading. In this way the apparatus never loses its monitoring vigilance, and because the absorbed radiation is determined by comparing the detection and reference beams, the measurement of the absorbing gas concentration remains unaltered.

According to a further aspect of the present invention, there is provided an apparatus for the remote quantitative monitoring of one or more selected gases in a gaseous environment, which comprises the apparatus herein specified characterised by the provision of means for varying according to a predetermined programme or in response to an external stimulus, the amount of radiation from the laser sources which is detected by the detector.

A preferred apparatus is one having means for varying the intensity of the combined beam which is directed at the various locations. This may vary the intensity abruptly, e.g. from full power to zero in a single step, or it may have the capacity to effect the variations smoothly from one intensity level to another.

A particularly preferred apparatus is one wherein the intensity varying means comprises means for varying the outputs of the laser sources. Alternatives include shutters for blocking or attenuating the laser radiation. The precise ways in which the outputs of the laser sources can be varied are dependent mainly on how the intensity variations are instigated.

One of our preferred ways of achieving the laser output variations according to a predetermined programme, is to use apparatus comprising position indicating means having a parameter which varies according to the orientation of the scanning means, programme means for storing a predetermined programme correlating the variations of radiation intensity with specific positions of the scanning means, trigger means for comparing the programme and the position of the scanning means and for providing a signal wherever the scanning means position and predetermined programme match, and a laser power control means responsive to signals from the trigger means.

For example, a simple electromechanical form of such apparatus may comprise an array of limit switches activated by a boss on the scanning mirror. The array, or more specifically the position of the switches in the array, provides the predetermined programme. The boss by providing a reference point whose position varies according to the orientation of the scanning means, is the position indicating means of this simple example, and the trigger means are provided by the switches themselves. As these become activated they provide signals to which the laser power control means can respond. In more sophisticated systems wherein overall control of the scanning is provided by computer, based on feedback signals from scanning mirror drive motors for example, the predetermined programme may be written into the computer program. However, the logic steps for comparing the feedback signals with the positions in the programme at which radiation intensity variation is required, are essentially the same as those for the electromechanical system.

An alternative way is to use the amount of radiation collected as an external stimulus, and a preferred apparatus for carrying this out comprises means for monitoring the electrical signals derived by the detector, reference means for providing a reference signal characteristic of a predetermined threshold level, a comparator for comparing the detector-derived signal with the reference signal, and a laser power control means connected to and responsive to the output from the comparator.

A particularly preferred apparatus is one which comprises the means for activating the laser power control means in response to the predetermined programme in addition to that in response to the variations in the amount of radiation collected.

The method and apparatus of the present invention are useful for monitoring gaseous pollutants in an industrial environment wherein the returned signal may regularly or randomly become uncharacteristically large, with corresponding risk of detector overload. Such uses, and the preferred methods and apparatus for such situations have been discussed at length above. However, there are other situations in which the present invention may be usefully employed. For example, in security applications, the apparatus may be used to detect vehicles driving within the scanned area by using a detection beam tuned to a wavelength absorbed by the exhaust gases of a vehicle e.g. using the $\nu=1$ to $\nu=0$ emission from a cooled carbon monoxide laser, which is absorbed by carbon monoxide. However, it may be desirable that the driver is not made aware of the monitor by sensing the radiation directed at him. These problems may be overcome or mitigated by the preferred method and apparatus of the present invention in which the radiation directed towards the locations by the apparatus is reduced to zero for at least one finite period during each cycle of the scanning operation.

Figure 2:
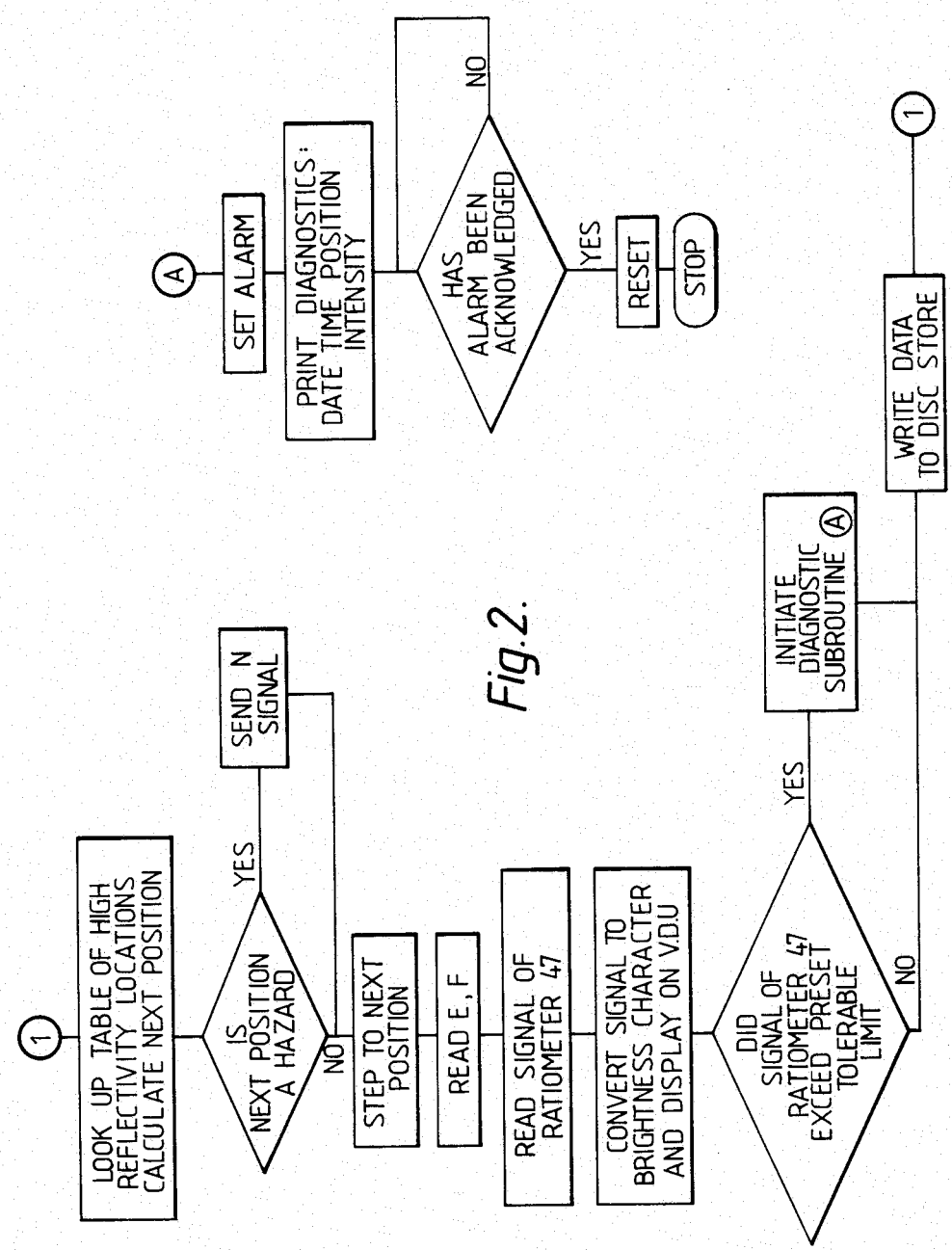

The invention is illustrated by reference to a specific embodiment thereof, shown in the accompanying drawings, in which:

FIG. 1 is a block diagram of an apparatus for monitoring ethylene in the atmosphere around a polyethylene plant and FIG. 2 is a simplified logic diagram to show visually the procedures described hereinafter for operating the apparatus.

The apparatus of FIG. 1 is that shown in FIG. 2 of our aforesaid European patent application, to which has been added features according to the present invention. These have been identified in the drawing by outlining them in broken lines. The apparatus comprises two uprated continuous mode carbon dioxide $C^{12}O_2^{16}$ lasers 31, 32 each having its own integral power supply and each being capable of emitting 40 W power. These provide respectively a detection beam at 9.673 $\mu$m (absorption coefficient=2.15 $cm^{-1}bar^{-1}$) and a reference beam at 9.619 $\mu$m (absorption coefficient=0.24 $cm^{-1}bar^{-1}$). The beam is passed through choppers 33, 34 with radiation reflected from the back of the chopper blades being directed to power meters 35, 36. The power meters 35, 36 continuously monitor the power output of the lasers 31, 32 and give out signals A and B which are a measure of the laser power. The choppers also give out signals C and D indicative of their rates of rotation and hence of the frequencies at which the respective beams are being chopped.

After modulation by the choppers, the beams are combined using a slab of germanium set at the Brewster angle and the combined beam is directed towards the various locations using a large mirror 37 of polished stainless steel positioned angularly with respect to the combined beam by two drive motors 38, 39 which tilt the mirror about a horizontal axis and about an axis perpendicular to that horizontal axis, respectively. The angular displacements are measured by shaft encoders on the drive units, and these measurements are given out as signals E and F respectively.

A small fraction of the radiation directed at the various locations is scattered back in the direction of the apparatus, and is reflected by the large mirror 37 onto a lens 40, which focusses the radiation directly onto liquid nitrogen cooled detector 41, having automatic topping-up means 42 for the cooling liquid. The output from the detector is divided and fed to two lock-in amplifiers 43, 44 taking signals C and D from the choppers to provide a continuous reference for the lock-in frequency. These amplifiers isolate the two modulated signals, which are smoothed and then corrected for power fluctuations in their respective originating lasers, by ratiometers 45, 46 using signals A and B from the power meters as their references. The corrected signals are then compared in a further ratiometer 47, and the ratio obtained is fed to a computer 48.

The computer effectively does two jobs. One is to compare the ratio signal from the ratiometer 47 with a preset standard representing the tolerable gas limit and to start an alarm 49 when the ratio drops below that limit, i.e. when the mass of gas exceeds the tolerable limit. The other purpose is to display on a visual display unit 50, a plan of the area of the polyethylene plant being scanned, superimposed with an indication of the level of ethylene detected, with a continuous updating of the display. To do this, the signals E and F from the mirror drives are input into the computer to give the orientation of the mirror 37 and hence provide the coordinates of the location on the plant to which the signal from the ratiometer 47 at any instant, relates.

The computer of this apparatus is also provided with a store 51 in the form of a floppy disc which records continuously the data fed to the visual display unit, the data being stored for a period of 75 minutes before being erased on the introduction of fresh data. This predetermined period was found to be convenient for this application in that it enabled a record of the build up of any leak to be analysed later.

The apparatus as so far described is the same as that described in the aforesaid European application. However, we have now added a monitor 60 which samples the output signal from the detector 41, and a reference signal generator 61 to provide a signal compatible with that from the monitor 60, the reference signal representing a threshold level of detector signal which is below the level at which overloading occurs. The reference signal generator is adjustable so that it can be set up during calibration of the apparatus to give a suitable threshold level, referred to in more detail below. The monitor and the reference signal generator are connected to a comparator 62, which is arranged to give a signal M whenever the monitor output exceeds the generator output. This is essentially an analogue signal, and increases with increases in the amount by which the detector signal exceeds the threshold level.

As mentioned above, the signals E and F provide the computer with the coordinates of the area being scanned. Under the present invention the computer is also provided with a two dimensional look-up table in which are stored the co-ordinates of permanent or semi-permanent areas of high reflectivity. The computer compares the values in the look-up table with the coordinates supplied by signals E and F, and provides a signal N when these match.

A laser power control unit 63 is provided to inject control signals into the servo units which are used to stabilise the lasers. The servo units are integral features of the laser 31, 32 so have not been shown separately. The laser power control unit is activated by the signals M and N from the comparator 62 and computer 48 respectively. The effects of these two signals are different but compatible.

The purpose of the N signal from the computer is to shut down the laser output completely for short periods which occur at the same position in each cycle. This control was provided mainly to avoid high-level radiation returned from supporting framework of the plant close to the apparatus, and between the apparatus and the parts of the plant where ethylene leaks might occur. Hence in this particular embodiment, on receipt of the signal N from the computer, the laser power control signals the servo unit to reduce the laser bias below its activation level. In this way, no overloading signal reaches the detector from these known areas of high reflectivity, this control relying entirely on the coordinates.

The purpose of the M signal is to take care of high levels of radiation which are collected unpredictably. By its very nature, the duration of such high level radiation is as unpredictable as its inception and position. It can therefore be important that monitoring of the gases should continue, and that normal service should be resumed as soon as possible. Thus on receipt of signal M, the laser power control 63 instructs the servo unit to reduce the power output of the laser sources, and to continue to do so while the M signal is being received. When the overload ceases the M signal ceases and the laser power winds back to its original level. Moreover, as mentioned above, the M signal is an analogue signal. This has the effect of increasing the rate at which the power output of the laser sources is reduced when the detector signal suddenly increases to a level considerably greater than the threshold level.

In order to demonstrate further the sequence of operations centered around the computer, we also provide in FIG. 2 a visual representation of the main operations described above for the scanning sequence.

In the specific apparatus described, the mirror is driven and the signals E and F provide the computer with the orientation of the mirrors. An alternative is for the computer to instruct the drive units what orientation to place the mirror into. It can be more elegant to control such functions than merely to monitor them, as the scanning operation can then also be initiated via the computer. However, during scanning the logic is essentially the same except that signals equivalent to E and F are sent out rather than E and F received.

What we claim is:

1. A method for the remote quantitative monitoring of one or more selected gases in a gaseous environment, which comprises the steps of generating electromagnetic radiation from laser sources to give at least one detection beam containing a specific absorption wavelength of the gas or gases being monitored and at least one reference beam having a wavelength that is significantly less strongly absorbed by the gas or gases being monitored, modulating the amplitude of each of the beams with different modulation frequencies or phases, combining the modulated beams into a single beam in which the component modulated beams are substantially coincident with one another, displacing the combined beam angularly through the gaseous environment so as to direct the combined beam towards a plurality of locations sequentially and repetitively, collecting at least a portion of the radiation which is reflected from each of the locations, deriving electrical signals corresponding to the intensity of the collected radiation, isolating the electrical signals corresponding to the intensity of the radiation having the aforesaid modulation frequencies or phases, obtaining a ratio of the isolated signals corresponding to radiation collected from a detection beam and a related reference beam thereby to provide a measure of the amount of the selected gas or gases in each beam path traversed by the collected radiation originating from the laser sources, and varying according to a predetermined programme or in response to an external stimulus, the amount of radiation from the laser sources which is detected by the detector thereby to prevent the detected amount from exceeding a predetermined level.

2. A method as claimed in claim 1 which comprises varying according to the predetermined programme or in response to the external stimulus, the amount of radiation reaching the detector from the laser sources.

3. A method as claimed in claim 2, which comprises monitoring the amount of radiation collected and varying the amount of radiation reaching the detector from the laser sources in response to the amousnt of radiation monitored.

4. A method as claimed in claim 3 in which, whenever the collected radiation exceeds a predetermined threshold, the amount of laser radiation reaching the detector is varied so as to remain within a predetermined range in excess of the threshold for so long as an excess of radiation is collected.

5. A method as claimed in any one of claims 2 to 4, in which the amount of radiation reaching the detector from the laser sources is varied by varying the amount of laser radiation which is directed at the locations.

6. A method as claimed in claim 1 in which the amount of radiation detected by the detector is varied by at least partially desensitising the detector in response to an increase in its output signal.

7. Apparatus for the remote quantitative monitoring of one or more selected gases in a gaseous environment, which comprises laser sources for generating electromagnetic radiation capable of being tuned to give at least one detection beam containing a specific absorption wavelength of the gas or gases to be monitored and at least one reference beam having a wavelength that is significantly less strongly absorbed by the gas to be monitored, means for modulating the amplitude of each of the beams with different modulation frequencies or phrases, means for combining the modulated beams into a single combined beam in which the component modulated beams are substantially coincident with one another, scanning means to displace the combined beam angularly through the gaseous environment so as to direct the combined beam towards a plurality of locations sequentially and repetitively, means for collecting at least a portion of the radiation which is returned from each of the locations, a detector for deriving electrical signals corresponding to the intensity of the collected radiation, means for isolating the electrical signals corresponding to the intensity of radiation having the aforementioned modulation frequencies or phases, means for obtaining the ratio of the isolated signals corresponding to radiation collected from a detection beam and a related reference beam thereby to provide a measure of the amount of the selected gas or gases in each beam path traversed between the apparatus and the scanned locations, means for indicating the amount of gas detected, and means for varying according to a predetermined programme or in response to an external stimulus, the amount of radiation from the laser sources which is detected by the detector thereby to prevent the detected amount from exceeding a predetermined level.

8. Apparatus as claimed in claim 7, having means for varying the intensity of the combined beam which is directed at the various locations.

9. Apparatus as claimed in claim 8 is one wherein the intensity varying means comprises means for varying the outputs of the laser sources.

10. Apparatus as claimed in claim 9 comprising position indicating means having a parameter which varies according to the orientation of the scanning means, programme means for storing a predetermined programme correlating the variations of radiation intensity with specific positions of the scanning means, trigger means for comparing the programme and the position of the scanning means and for providing a signal wherever the scanning means position and predetermined programme match, and a laser power control means responsive to signals from the trigger means.

11. Apparatus as claimed in any one of claims 7 to 9 comprising means for monitoring the electrical signals derived by the detector, reference means for providing a reference signal characteristic of a predetermined threshold level, a comparator for comparing the detector-derived signal with the reference signal, and a laser power control means connected to and responsive to the output from the comparator.

12. Apparatus as claimed in claim 11 which comprises means for activating the laser power control means in reponse to a predetermined programme in addition to that in response to the variations in the amount of radiation collected.

* * * * *